(12) United States Patent
Dastager et al.

(10) Patent No.: US 11,858,885 B2
(45) Date of Patent: Jan. 2, 2024

(54) CELLULOSIC COMPLEX AND APPLICATIONS THEREOF

(71) Applicant: Council of Scientific & Industrial Research, New Delhi (IN)

(72) Inventors: Syed Gulam Dastager, Pune (IN); Madhukar Shyam Said, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 87 days.

(21) Appl. No.: 17/441,467

(22) PCT Filed: Mar. 24, 2020

(86) PCT No.: PCT/IN2020/050274
§ 371 (c)(1),
(2) Date: Sep. 21, 2021

(87) PCT Pub. No.: WO2020/202179
PCT Pub. Date: Oct. 8, 2020

(65) Prior Publication Data
US 2022/0153669 A1  May 19, 2022

(30) Foreign Application Priority Data
Mar. 29, 2019  (IN) .............. 201911012428

(51) Int. Cl.
| C07C 41/22 | (2006.01) |
| C08B 15/00 | (2006.01) |
| C08B 31/00 | (2006.01) |
| C08B 37/00 | (2006.01) |

(52) U.S. Cl.
CPC .............. *C07C 41/22* (2013.01); *C08B 15/00* (2013.01); *C08B 31/00* (2013.01); *C08B 37/0045* (2013.01)

(58) Field of Classification Search
CPC ......... C07C 41/22; C08B 15/00; C08B 31/00; C08B 37/0045; C08B 2100/11
USPC ..................................... 536/1.11, 2
See application file for complete search history.

(56) References Cited

PUBLICATIONS

Kim et al, Angew Chem, 2008, 120, 8532-8534.*
Engle et al, Chem Sci 2015, 6, 5293-5302.*
Thorat et al, RSC Adv., 2018, 8, 29797-29805.*
International Search Report dated Jun. 29, 2020 in reference to co-pending Indian Patent Application No. PCT/IN2020/050274 filed Mar. 24, 2020.
Written Opinion dated Jun. 29, 2020 in reference to co-pending Indian Patent Application No. PCT/IN2020/050274 filed Mar. 24, 2020.
Kim, et al., "Terabutylammonium Tetra(ter-Butyl Alcohol)-Coordinated Fluoride as a Facile Fluoride Source", vol. 120, pp. 8532-8534, 2008.
Engle, et al., "Coordination diversity in hydrogen-bonded homoleptic fluoride-alcohol complexes modulates reactivity", Chem. Science, vol. 6, pp. 5293-5302, 2015.
Thorat, et al., "High yield production of cellulose by a Komagataeibacter rhaeticus PG2 strain isolated from pomegranate as a new host", Royal Society of Chemistry, vol. 8, pp. 29797-29805, 2018.
Machado, et al., "Komagataeibacter rhaeticus as an alternative bacteria for cellulose production", Carbohydrate Polymers, vol. 152, pp. 841-849, 2016.

* cited by examiner

*Primary Examiner* — Ganapathy Krishnan
(74) *Attorney, Agent, or Firm* — Dinsmore & Shohl LLP

(57) ABSTRACT

The present invention provides a polysaccharide supported fluorinating agents which can be used in fluorination reactions. The invention particularly describes a new bacterial cellulose supported tetra-n-butyl ammonium fluoride complex [$NBu_4$(Bac-Cell-OH)F] which is stable and non-hygroscopic. The invention further relates to a process for fluorination using the [$NBu_4$(Bac-Cell-OH)F] complex.

8 Claims, 4 Drawing Sheets

1 2 3 4 5

CELLULOSIC COMPLEX AND APPLICATIONS THEREOF

CROSS-REFERENCES TO RELATED APPLICATIONS

This application is a national-stage application under 35 U.S.C. § 371 of International Application No. PCT/IN2020/050274, filed Mar. 24, 2020, which International Applications claims benefit of priority to Indian Patent Application No. 201911012428, filed Mar. 29, 2019.

TECHNICAL FIELD

The invention relates to polysaccharide supported tetra-n-butyl ammonium fluoride complexes. More particularly, the present invention provides a stable, non-hygroscopic cellulosic complexes with fluorinating agent, which can be used in fluorination reactions.

BACKGROUND

Fluorination reactions are of critical importance, because Fluorine is the one of the key elements present in the most of the molecules of pharmaceutical, agrochemical, and material industries. 30% of the new drugs being discovered contain F as one of their elements.

Introducing the fluorine atom in the organic backbone is very challenging because of the small size and low solubility of the fluoride salts in most of the organic solvents. Also, fluorine atom interacts with other functional groups present in the organic structure like esters, alcohols, amides etc through hydrogen bonding and prevent its insertion. Fluoride salts are highly basic in nature and solvation effect reduces their nucleophilic characteristics. Due to hygroscopic nature and lack of hydrogen-bond contributor, fluoride basicity can override its nucleophilicity and lead to unwanted side reactions. Hence the hydrogen bonding acts as an amplifier to increase the nucleophilicity of the fluorine atoms.

Tetra alkyl ammonium fluoride salts are commonly used in the fluorination reaction, but these salts are extremely hygroscopic, possess low thermal stability and are mostly available in their hydrated form, which has very poor nucleophilic characteristics. The poor stability profile of Tetra alkyl ammonium fluoride salts has created a need to provide more stable fluoride salts to conduct fluorination reactions.

Very few reports are present in literature for synthesizing the bench stable fluorine complexes or reagent. Recently scientists have synthesized more stable, less hygroscopic fluorine complexes from fluoride-tert-butyl alcohol complex, fluoride-alcohol complex and fluoride-diaryluria complex. These complexes are stable through their NH—F and OH—F hydrogen bonding. However, while being used as a fluorinating agent, they lack specificity and result in formation of undesired side products.

Hence there is a need in the art for stable fluorinating agents that provide desired fluorinated compounds with a high level of specificity.

OBJECTS OF THE INVENTION

An object of the invention is to provide a simple stable cellulosic complex with fluorinating agent.

Another object of the invention is to provide stable cellulosic complex with fluorinating agent that can effect fluorination reactions with a high selectivity towards desired fluorinated products.

SUMMARY

Accordingly, the present invention provides a stable polysaccharide supported complex with fluorine compounds as a new fluorinating agent. More particularly, the present invention provides a new bacterial cellulosic complex with TBAF fluorinating agent for the fluorination reactions.

In an embodiment, the polysaccharides are selected from plant cellulose, bacterial cellulose, starch and pectin. In a preferred embodiment, the cellulose is bacterial celluloses.

In another embodiment, the stable polysaccharide supported TBAF complexes are non-hygroscopic.

The stable polysaccharide supported TBAF complexes are useful as a fluorinating agent and they facilitate the formation of the desired fluorinated products with a high degree of selectivity, with minimal formation of undesired products.

ABBREVIATIONS USED

| Sr. No | Name | Abbreviation |
|---|---|---|
| 1 | TBAF | Tetra-n-butyl ammonium fluoride |
| 2 | Pectin- TBAF Complex | $NBu_4(Pec-OH)F$ |
| 3 | Plant Cellulose- TBAF Complex | $NBu_4(Pla-cell-OH)F$ |
| 4 | Bacterial Cellulose- TBAF Complex | $NBu_4(Bac-cell-OH)F$ |
| 5 | Starch- TBAF Complex | $NBu_4(Sta-OH)F$ |
| 6 | Standard fluorination complex | $NBu_4F$ |
| 7 | Literature reported fluorination complex | $NBu_4(tert-Bu—OH)F$ |

DETAILED DESCRIPTION

Herein, the inventors have synthesized polysaccharide supported TBAF as a stable complex and disclosed its application in aliphatic SN2 fluorination. The present invention provides natural polysaccharide and TBAF complexes in their w/w ratio ranging from 1:0.3 to 1:5. The polysaccharide is selected from the group comprising of pectin, bacterial cellulose, plant cellulose and starch.

In embodiment, the complex is synthesized by a process comprising:
a) adding Tetrabutylammonium fluoride hydrate and polysaccharide in their respective equivalent amount (w/w) to hexane;
b) refluxing mixture of step (a) in inert atmosphere at 80° C. for 1.5 h with vigorous stirring;
c) cooling the solution of step (b) to a temperature in the range of 25-30° C., filtering, washing with hexane and drying under high vacuum at a temperature in the range of 25-30° C. to obtain the desired tetrabutylammonium fluoride/polysaccharide complex.

The TBAF polysaccharide complexes of the invention thus synthesized are stable, non-hygroscopic and recyclable.

Figure 1:
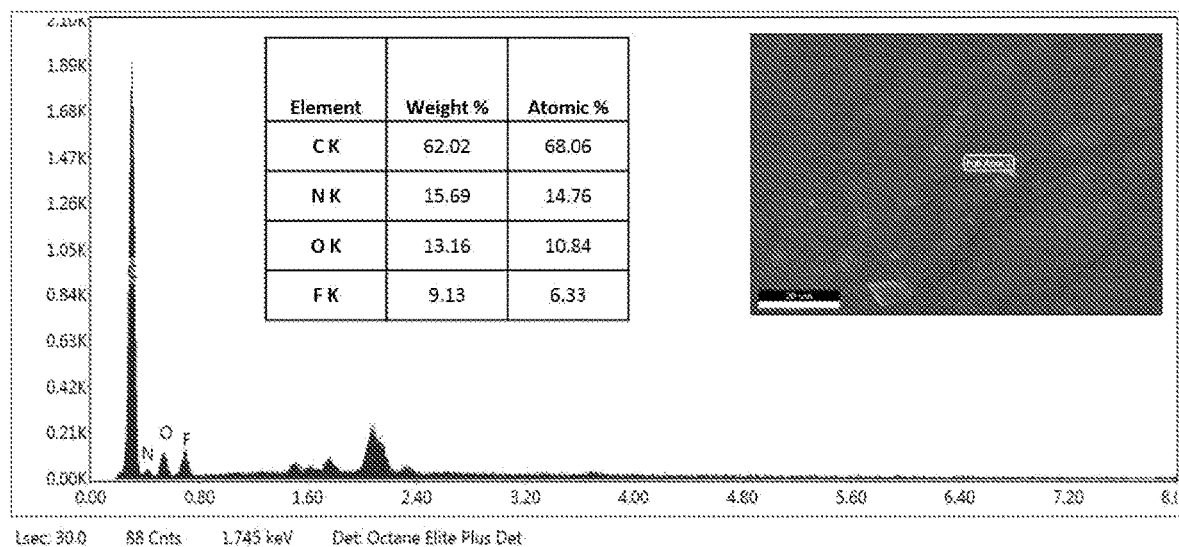
FIG. 1: SEM of $NBu_4(Bac-cell-OH)F$
Figure 2:
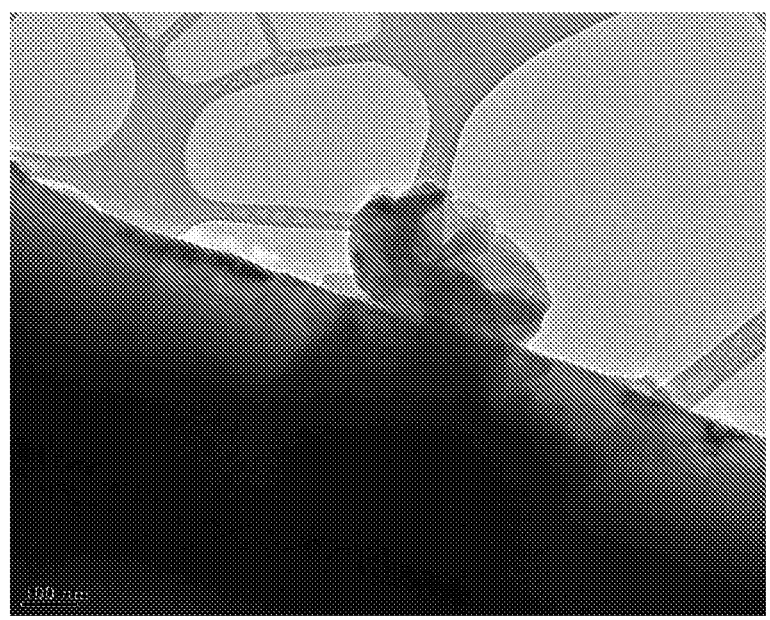
FIG. 2: TEM image of $NBu_4(Bac-cell-OH)F$

In an aspect of the embodiment, the TBAF polysaccharide complexes have been characterized using SEM and TEM images, refer FIGS. 1 and 2. In the SEM images, white dots are observed, confirming the loading of TBAF in the polysaccharides. The TEM images show the special threading of TBAF observed with bacterial cellulose.

Figure 3:
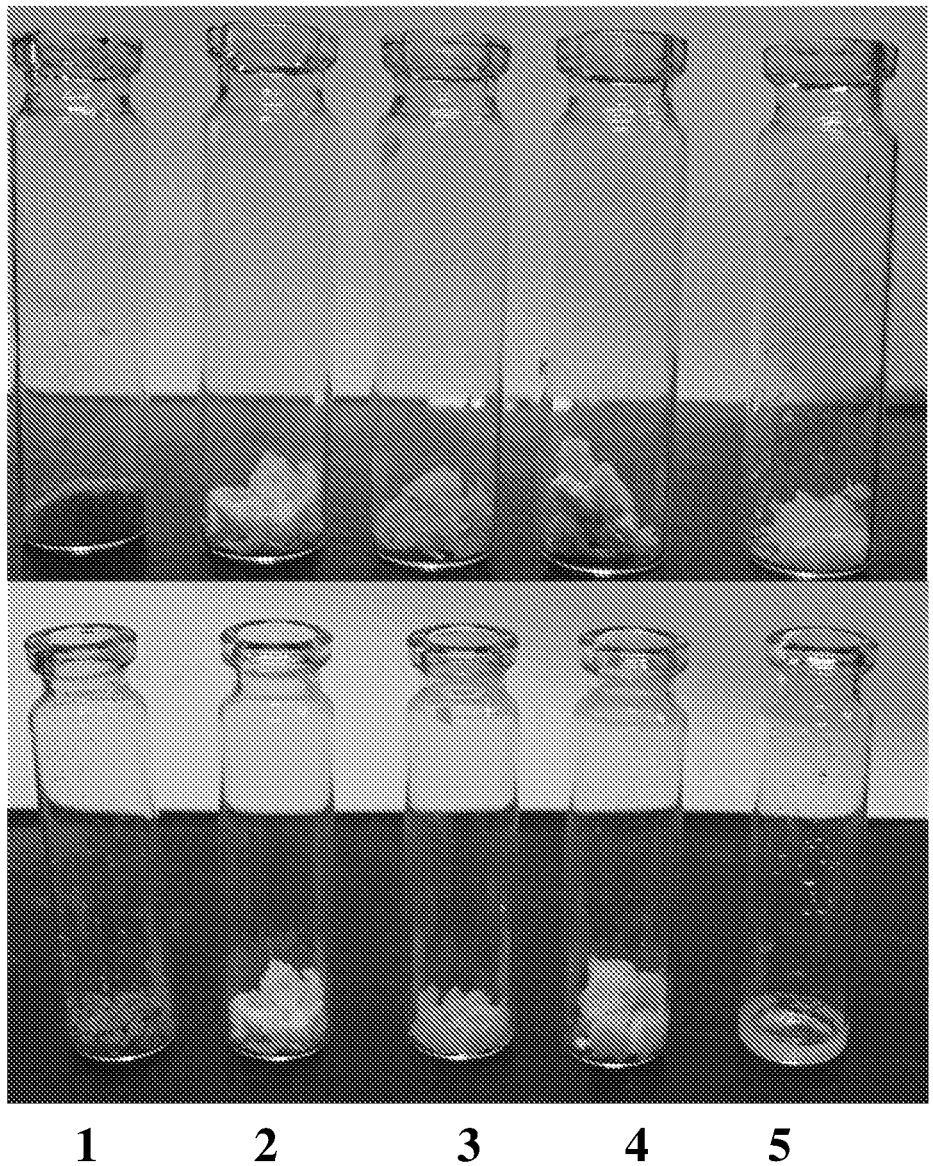
FIG. 3: Demonstration of the hygroscopicity of
1. $NBu_4(Pec-OH)F$
2. $NBu_4(Bac-OH)F$
3. $NBu_4$ (Pla-cell-OH)F
4. $NBu_4$ (Sta-cell-OH)F
5. $NBu_4F$
Figure 4:
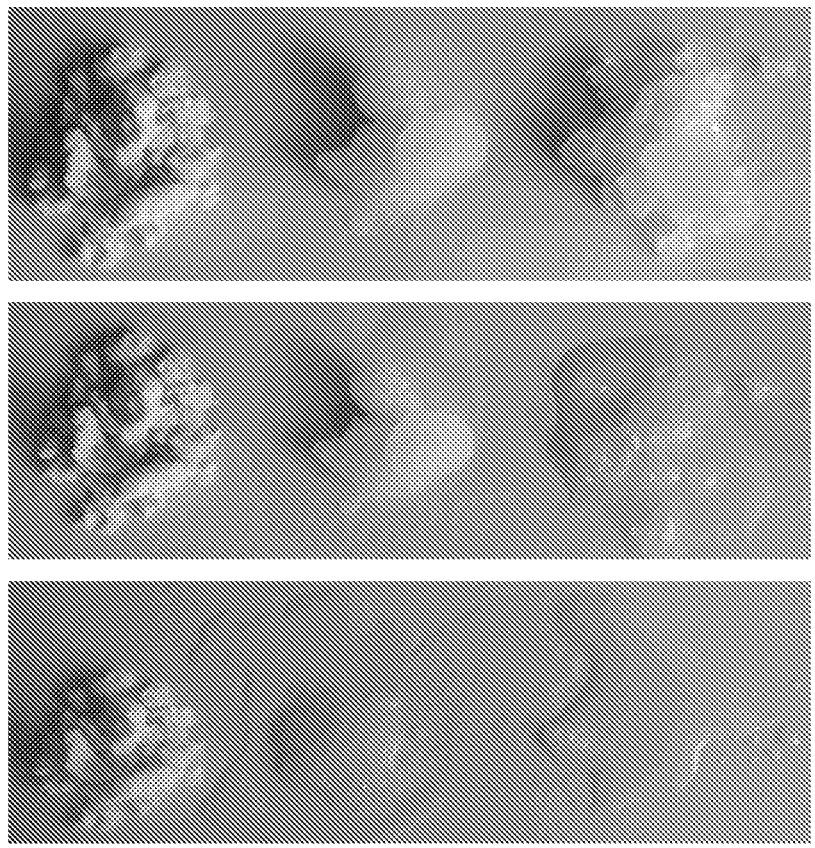
FIG. 4: Demonstration of the hygroscopicity
1. $NBu_4(Bac-OH)F$
2. $NBu_4(tert-Bu-OH)F$
3. $NBu_4F$

In another aspect of the embodiment, the hygroscopicity of the complexes were evaluated by exposing the complexes at room temperature. After 15 minutes to 2 hours, the complexes were examined visually and the results are shown in FIG. 3. The top row indicates the visual comparison after exposure for 15 minutes while the bottom row is after two hours of exposure. The reported TBAF complex is hygroscopic and became a liquid within 15 minutes, while the bacterial cellulosic-TBAF complexes remained stable up to two hours, without being liquefied. The study was continued and the disclosed complexes were found to be stable for 21 days.

In another embodiment, the present invention provides the polysaccharide supported TBAF complex is used as a fluorinating agent and can be used for the fluorination of antibiotics, cancer drugs, sugars, steroids, pesticides, herbicides, and fungicide. The complexes provide 40-99% selectivity towards desired product, with minimal side product formation.

In an embodiment, the fluorination reactions using the complexes give selectivity towards desired products on recycling the complex up to 4 times. The general process for the fluorination reaction comprises the steps of:
i) charging substrate compound and complex in 1:1.5 w/w ratio into acetonitrile solvent;
ii) stirring the reaction mixture of step i) at a temperature in the range of 65-70° C. for 3 hrs;
iii) cooling the reaction mixture from step ii) to a temperature in the range of 25-35° C., filtering and washing with ethyl acetate solvent;
iv) removing the solvent from the reaction mixture obtained at step iii) under reduced pressure;
v) purifying the obtained compound at step iv) with flash chromatography by using 20% ethyl acetate in hexane eluent to afford pure fluorinated compound.

The representative process for the fluorination of compound 5 is depicted below in scheme-1; wherein X is good leaving group to be replaced with fluorine.

Scheme-1

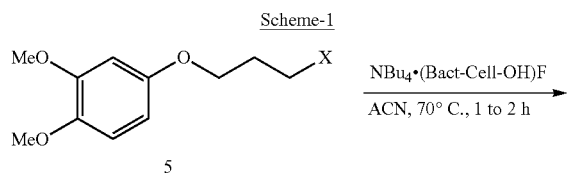

X = OMs, OTs, OTf, I, Br

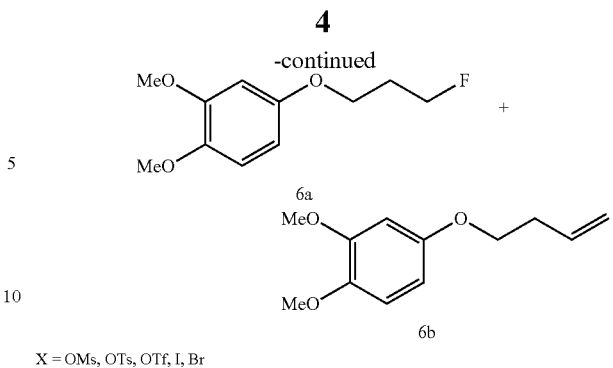

Table-1 below summarizes the results obtained by using different mole ratios of bacterial cellulose-TBAF complex at different time intervals. 3-(3,5-dimethoxyphenoxy) propyl methane sulphonate (5a) is used as a substrate and compounds 1-(3-fluoropropoxy)-3,5-dimethoxybenzene (6a) and 1-(allyloxy)-3,5-dimethoxy benzene (6b) are the fluorination products.

TABLE 1

| Entry No | NBu$_4$(Bac-cell-OH)F. | Solvent | Time (h) | Yield[c] 6a | 6b |
|---|---|---|---|---|---|
| 1 | 1 | CH$_3$CN | 2 | 90 | — |
| 2 | 1.5 | CH$_3$CN | 2 | 92 | — |
| 4 | 2 | CH$_3$CN | 2 | 88 | trace |
| 5[d] | 2 | CH$_3$CN | 1.5 | 87 | 14 |
| 6 | 2 | CH$_3$CN | 1 | 85 | 13 |
| 7 | 2 | CH$_3$Ph | 2 | 71 | 19 |
| 8[e] | 2 | CH$_3$CN | 2 | 81 | 9 |

[a]All reactions were carried out on a 1.0 mmol scale of substrate in solvent (8.0 mL) at 70° C.
[b]Fluorine complex used equivalent ratio of TBAF (Use 2 eq. of TBAF loaded in 1 eq. bacterial cellulose i.e. 100% of TBAF).
[c]Isolated yields.
[d]Reaction carried at 90° C.
[e]Reaction carried in an open atmosphere.
— not detected.

Referring to the scheme-1 and table 1, the fluorination reaction was conducted with bacterial cellulose-TBAF complex using acetonitrile or tri methyl benzene as a solvent at 50-100° C. for a substrate: complex ratio of 1:1 to obtain more that 70% selectivity of desired fluorinated product. The complex used is in the range of 1:1 to 1:2 of TBAF: cellulose. In a preferred embodiment, the cellulose is bacterial cellulose.

Table 2 below summarizes the results obtained by using recycled complex. It is found that the complex can be recycled up to 4 times. After completion of reaction, the reaction mass is cooled to 25-35° C. and bacterial cellulose is filtered. It is further washed with ethyl acetate and dried under high-vacuum (2 mbar) to re-use for further loading of TBAF to form complex for further reactions.

TABLE 2

| Entry | Loading of TBAF | Yield of fluorinated product |
|---|---|---|
| 1 Recycling | 70% loading of TBAF | 94% |
| 2 Recycling | 68% loading of TBAF | 94% |
| 3 Recycling | 68% loading of TBAF | 93% |
| 4 Recycling | 66% loading of TBAF | 94% |

The invention will now be described with reference to examples, which should not be construed to limit the invention in any manner.

Examples

Following examples are given by way of illustration and therefore should not be construed to limit the scope of the invention.

Example A: General Procedure for the Synthesis of Polysaccharide Sported TBAF Complex (A)

To a flame-dried round bottom flask with cooling condenser Tetrabutylammonium fluoride hydrate and polysaccharide (Pectin, Starch and plant cellulose were procured from Sigma, whereas bacterial cellulose was synthesized in the lab by indigenous bacteria which inventors have isolated, refer RSC Advances, 2018, 8, 29797-29805, DOI: 10.1039/c8ra05295f) was added in their respective equivalent amount (w/w) in 100 ml of hexane. This mixture was refluxed in nitrogen atmosphere at 80° C. for 1.5 h with vigorous staring. During the reaction, complex shows the water droplets on sidewall of the condenser, which indicates the completion of the reaction and complex formed. The solution was allowed to cool to 25-30° C., filtered, washed with hexane and dried under high vacuum at 25-35° C. to give the desired tetrabutylammonium fluoride/polysaccharide complexes which was used for the aliphatic nucleophilic fluorination.

In this manner complexes were prepared with polysaccharides such as pectin, starch, bacterial cellulose and plant cellulose in the ratios 1:0.1 to 1:5 w/w of polysaccharide:TBAF.

Example 1: Preparation and Characterization of Pectin+TBAF Complex: NBu$_4$(Pec-OH)F

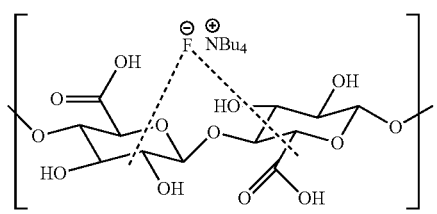

| Sr. No | Loading (%)w/w | | Result |
|---|---|---|---|
| | Pectin | TBAF | |
| 1 | 1 | 1 | Solid |
| 2 | 1 | 2 | Sticky Solid |
| 3 | 1 | 3 | Sticky Solid |

Example 2: Preparation and Characterization of Bacterial Cellulose+TBAF Complex: NBu$_4$(Bac-Cell-OH)F

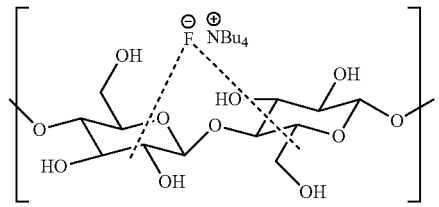

| Sr. No | Loading (%)w/w | | Result |
|---|---|---|---|
| | Cellulose | TBAF | |
| 1 | 1 | 1 | Solid |
| 2 | 1 | 2 | Solid |
| 3 | 1 | 3 | Solid |
| 4 | 1 | 4 | Solid |
| 5 | 1 | 5 | Slightly Sticky Solid |
| 6 | 1 | 6 | Sticky Solid |

Example 3: Preparation of Characterization of Plant Cellulose+TBAF Complex: NBu$_4$(Pla-Cell-OH)F

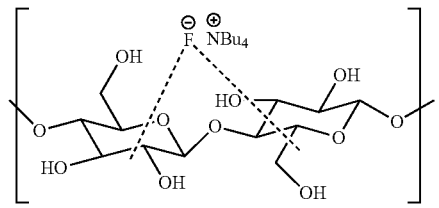

| Sr. No | Loading (%)w/w | | Result |
|---|---|---|---|
| | Cellulose | TBAF | |
| 1 | 1 | 1 | Gel |
| 2 | 1 | 0.9 | Gel |
| 3 | 1 | 0.8 | Gel |
| 4 | 1 | 0.7 | Sticky Solid |
| 5 | 1 | 0.6 | Sticky Solid |
| 6 | 1 | 0.5 | Sticky Solid |
| 7 | 1 | 0.4 | Sticky Solid |
| 8 | 1 | 0.3 | Solid |

Example 4: Preparation of Characterization of Starch+TBAF Complex: NBu₄(Sta-Cell-OH)F

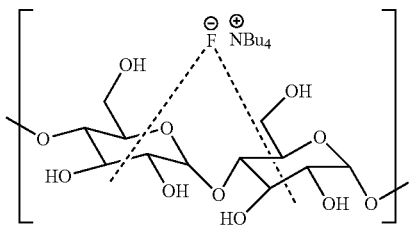

| Sr. No | Loading (%)w/w Cellulose | TBAF | Result |
|---|---|---|---|
| 1 | 1 | 1 | Gel |
| 2 | 1 | 0.9 | Gel |
| 3 | 1 | 0.8 | Gel |
| 4 | 1 | 0.7 | Gel |
| 5 | 1 | 0.6 | Sticky Solid |
| 6 | 1 | 0.5 | Sticky Solid |
| 7 | 1 | 0.4 | Sticky Solid |
| 8 | 1 | 0.3 | Solid |

Example B: A Representative Fluorination Procedure synthesis of 4-(3-fluoropropoxy)-1,2-dimethoxybenzene: In a flame dried round bottom flask, mesylated substrate compound (0.290 mg, 1 mmol) and NBu₄(Bac-cell-OH)F.1 (0.3915 mg, 1.5 eq) in dry Acetonitrile were taken and the reaction vial was flushed with N2 and stirred at 70° C. for 3 h. Cooled reaction mixture was filtered using sintered funnel. The reaction mixture was washed with ethyl acetate and evaporated under reduced pressure. The crude product was purified by flash column chromatography using (20% EtOAc/hexane) to give corresponding fluorinated compound. 4-(3-fluoropropoxy)-1, 2-dimethoxybenzene.

4-(3-fluoropropoxy)-1,2-dimethoxybenzene: $^1$H NMR (400 MHz, CDCl₃) δ 6.10 (s, 3 H), 4.71 (t, 0.1=5.8 Hz, 1 H), 4.59 (t, 0.1=5.8 Hz, 1 H), 4.07 (t, J=6.1 Hz, 2 H), 3.78 (s, 6 H), 2.25-2.08 (m, 2 H). $^{13}$C NMR (101 MHz, CDCl₃) δ 161.5, 160.6, 93.3, 93.1, 80.4 (d, J=164.15 Hz), 63.5, (d, J=4.62 Hz), 55.3, 30.4 (d, 0.1=20.04 Hz). $^{19}$F NMR (400 MHz, CDCl₃) δ 222.14

A similar procedure was followed for different substrates to obtain following fluorinated products.
2-fluoro-1-(3-methoxyphenyl)ethan-1-one:

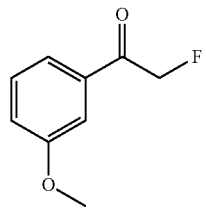

$^1$H NMR (400 MHz, CDCl₃) δ 7.45 (d, J=2.3 Hz, 1H), 7.43-7.38 (m, 2H), 7.19-7.15 (m, 1H), 5.52 (d, J=46.71 Hz, 2H), 3.87 (s, 3H); $^{13}$C NMR (101 MHz, CDCl₃) δ 193.1, (d, J=15.33 Hz), 160.0, 134.9, 129.9, 120.6, 120.6, (d, J=2.8 Hz), 112.1, (d, J=1.93 Hz), 84.5, (d, J=182.11 Hz), 55.5; $^{19}$F NMR (400 MHz, CDCl₃) δ 232.60.

$^1$H NMR (400 MHz, CDCl₃) δ 7.87 (d, J=8.2 Hz, 2H), 7.49 (d, J=8.7 Hz, 2H), 5.49 (d, J=46.71 Hz, 2H); $^{13}$C NMR (101 MHz, CDCl₃) δ 192.5 (d, J=15.33 Hz), 140.7, 132.1, 129.4 (d, J=2.88 Hz), 129.3, 84.6 (d, 0.1=184.03 Hz); $^{19}$F NMR (400 MHz, CDCl₃) δ 232.60.

1-fluorododecane:

$^1$H NMR (400 MHz, CDCl₃) δ 4.50 (t, J=6.1 Hz, 1H), 4.39 (t, J=6.1 Hz, 1H), 1.75-1.63 (m, 2 H), 1.28 (m., 18 H), 0.89 (t, J=6.1 Hz, 2H); $^{13}$C NMR (101 MHz, CDCl₃) δ 84.2 (d, 0.1=163.68 Hz), 31.9, 30.4 (d, J=19.27 Hz,) 29.6, 29.6, 29.5, 29.4, 29.3, 25.2, 25.1, 22.7, 14.1; $^{19}$F NMR (400 MHz, CDCl₃) δ 232.60.

1-fluoropentadecane:

$^1$H NMR (400 MHz, CDCl₃) δ 4.50 (t, J=6.1 Hz, 1H), 4.39 (t, J=6.1 Hz, 1H), 1.80-1.61 (m, 2H), 1.44-1.26 (m, 24H), 0.90 (t, J=6.1 Hz, 2H); $^{13}$C NMR (101 MHz, CDCl₃) δ 84.2 (d, J=164.15 Hz), 31.9, 30.4 (d, J=19.25 Hz), 29.7, 29.6, 29.5, 29.4, 29.3, 25.2, 25.1, 22.7, 14.1; $^{19}$F NMR (400 MHz, CDCl₃) δ 232.60.

9-(2-fluoroethyl)-9H-carbazole:

$^1$H NMR (400 MHz, CDCl₃) δ 8.16 (d, J=7.9 Hz, 2H), 7.55-7.48 (m, 2H), 7.47-7.42 (m, 2H), 7.35-7.28 (m, 2H), 4.87 (t, J=5.4 Hz, 1H), 4.75 (t, J=4.88 Hz, 1H), 4.64 (t, J=5.41 Hz, 1 H), 4.63 (t, J=4.8 Hz, 1 H); $^{13}$C NMR (101 MHz, CDCl₃) δ 140.4, 125.8, 123.0, 120.4, 119.3, 108.5, 81.9 (d, J=172.6 Hz,), 43.2, (d, J=22.3 Hz); $^{19}$F NMR (400 MHz, CDCl₃) δ 232.60.

2-benzyl-4-chloro-1-(3-fluoropropoxy)benzene:

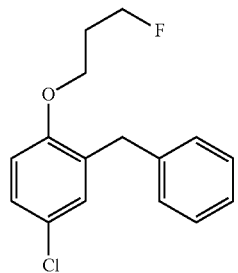 [SMILES: FCCCOc1ccc(Cl)cc1Cc1ccccc1]

$^1$H NMR (400 MHz, CDCl$_3$) δ 7.33-7.26 (m, 2H), 7.26-7.13 (m, 4H), 7.09 (d, J=2.7 Hz, 1 H), 6.79 (d, J=8.7 Hz, 1H), 4.58 (t, J=5.7 Hz, 1H), 4.46 (t, J=6.0 Hz, 1 H), 4.06 (t, J=6.0 Hz, 2H), 3.95 (s, 2H), 2.19-2.06 (m, 2H)$^3$C NMR (101 MHz, CDCl$_3$) δ 155.1, 140.1, 131.5, 130.3, 128.7, 128.4, 127.1, 126.1, 125.4, 1 12.3, 80.4, (d, J=164.86 Hz), 63.8 (d, J=4.79 Hz), 30.4, (d, J=20.13 Hz); $^{19}$F NMR (400 MHz, CDCl$_3$) δ 232.60.

1-(3-fluoropropoxy)-1H-benzo[d][1,2,3]triazole:

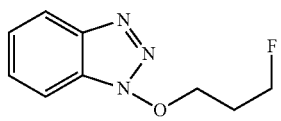 [SMILES: FCCCOn1nnc2ccccc21]

$^1$H NMR (400 MHz, CDCl$_3$) δ 7.51 (d, J=2.3 Hz, 1H), 7.33 (dd, J=2.3, 8.7 Hz, 1H), 6.82 (d, J=8.7 Hz, 1H). 4.76 (t, J=5.7 Hz, 1H), 4.64 (t, J=5.7 Hz, 1H), 4.14 (t, J=6.0 Hz, 2 H), 2.27-2.17 (m, 2 H); $^{13}$C NMR (101 MHz, CDCl$_3$) δ 153.6, 132.7, 130.5, 124.1, 114.6, 112.8, 80.4 (d, J=164.85 Hz), 64.9, (d, J=4.79 Hz), 30.2 (d, J=20.13 Hz); $^{19}$F NMR (400 MHz, CDCl$_3$) δ=232.60.

1-([1,1'-biphenyl]-4-yl)-2-fluoroethan-1-one:

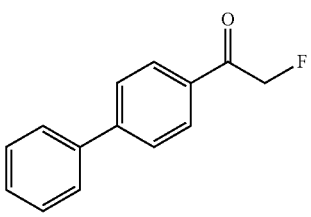 [SMILES: O=C(CF)c1ccc(-c2ccccc2)cc1]

$^{13}$C NMR (101 MHz, CDCl$_3$) δ 193.0, (d, J=15.34 Hz 146.8, 139.5, 132.3, 129.0, 128.5, 128.4, 127.5, 127.2, 127.1, $^{19}$F NMR (400 MHz, CHLOROFORM-d) δ=232.60.

(6S)-4-(2,2-dimethyl-1,3-dioxolan-4-yl)-6-fluoro-2,2-dimethyltetrahydrofuro[3,4-d][1,3]dioxole:

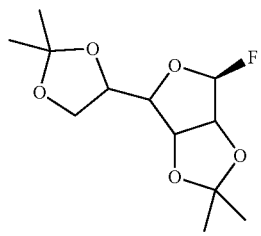 [SMILES: CC1(C)OCC(C2O[C@@H](F)C3OC(C)(C)OC23)O1]

$^1$H NMR (400 MHz CDCl$_3$) δ 5.59 (d, J=59.51 Hz 1 H), 4.86 (dd, J=3.5, 5.3 Hz, 1H), 4.78 (t, J=6.1 Hz, 1 II), 4.44-4.38 (m, 1 H), 4.17 (dd, J=3.1, 7.6 Hz, 1 H), 4.12 (dd, J=6.10, 8.39 Hz, 1H), 4.09-4.05 (dd, J=4.4, 8.39 Hz, 1H), 1.46 (d, J=2.3 Hz, 6H), 1.39 (s, 3H), 1.35 (s, 3 H); $^{13}$C NMR (101 MHz, CDCl$_3$) δ 114.7, 113.7 (d, J=69.09 Hz) 109.4, 84.7 (d, J=42.17 Hz) 82.6, 78.6, 72.7, 66.6, 26.9, 25.8, 25.1, 24.5; $^{19}$F NMR (400 MHz, CDCl$_3$) δ 232.60.

3-Fluorostigmasterol:

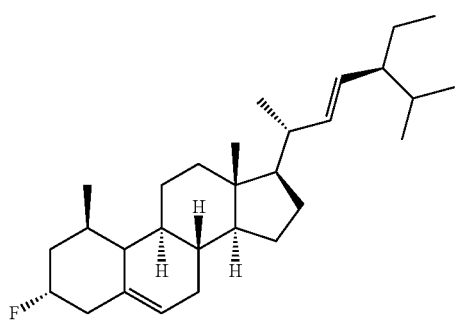

$^1$H NMR (500 MHz, CDCl$_3$) δ 5.34 (d, J=5.0 Hz, 1H), 5.19-5.14 (m, 1H), 5.02 (dd, J=8.6, 15.1 Hz, 1H), 3.34-3.23 (m, 1H), 2.30 (dd, J=2.9, 13.2 Hz, 1H), 2.27-2.20 (m, 1H), 2.10-1.95 (m, 5H), 1.88-1.82 (m, 2H), 1.74-1.69 (m, 1H), 1.58 (s, 3H), 1.55-1.45 (m, 8H), 1.27 (d, J=7.2 Hz, 2H), 1.20-1.15 (m, 3H), 1.01 (s, 4H), 0.85 (d, J=6.1 Hz, 3H), 0.81 (d, J=7.6 Hz, 7H), 0.70 (s, 3 H); $^3$C NMR (126 MHz, CDCl$_3$) δ 141.3, 138.3, 129.2, 121.3, 56.5 (d, J=116.34 Hz), 51.2, 50.3, 42.2, 40.5, 40.0, 39.7, 37.4, 36.9, 31.9, 31.9, 29.4, 28.9, 25.4, 24.4, 21.2, 21.1, 19.4, 19.0, 12.2, 12.0; $^{19}$F NMR (400 MHz, CDCl$_3$) δ 232.60.

Example C: General Process for the Recovery of the Complex for Recycling

After completion of the reaction, the reaction mixture was cooled to 25-35° C. bacterial cellulose was filtered, washed with ethyl acetate and dried under high-vacuum (2 mbar) to re-use for further loading if TBAF.

Advantages of the Invention

Stable complex
Non hygroscopic
Complex is recyclable
Complex provides good selectivity of fluorinated product

The invention claimed is:

1. A non-hygroscopic, recyclable, and thermally stable complex, the complex comprising a polysaccharide support and tetra-n-butyl ammonium fluoride complexed to the polysaccharide support, wherein the w/w ratio of the polysaccharide support to the tetra-n-butyl ammonium fluoride in the complex is from 1:0.3 to 1:6, and wherein the polysaccharide support of the fluoride complex is recyclable as a fluorinating agent.

2. The non-hygroscopic, recyclable, and thermally stable complex of claim 1, wherein the polysaccharide support is selected from pectin, bacterial cellulose, plant cellulose, or starch.

3. The non-hygroscopic, recyclable, and thermally stable complex of claim 1, wherein the polysaccharide support is a bacterial cellulose obtained from a *Komagataeibacter rharticus* PG2 strain isolated from a pomegranate host, the bacterial cellulose having a crystallinity index of 80.80 as measured using XRD and a nano-fibrillar width from 30 nm to 80 nm as measured using scanning electron microscopy.

4. The non-hygroscopic, recyclable, and thermally stable complex of claim 3, wherein the w/w ratio of the bacterial cellulose support to the tetra-n-butyl ammonium fluoride is 1:3.

5. A process for the preparation of a non-hygroscopic, recyclable,
and thermally stable complex according to claim 1, the process comprising:
(a) adding a polysaccharide support and tetra-n-butyl ammonium fluoride hydrate at a w/w ratio of 1:0.3 to 1:6 in hexane to obtain a mixture;
(b) refluxing the mixture obtained in (a) under inert atmosphere at 80° C. for 1.5 hours with vigorous stirring to obtain a solution;
(c) cooling the solution obtained in (b) to 25-30° C., filtering, washing with hexane followed by drying under high vacuum to obtain the non-hygroscopic, thermally stable complex.

6. A process for obtaining a fluorinated compound using the non-hygroscopic, recyclable, and thermally stable complex according to claim 1, the process comprising:

(i) charging a substrate compound and the complex in a w/w ratio from 1:1 to 2:1 into a solvent to obtain a reaction mixture;
(ii) stirring the reaction mixture obtained in (i) at a temperature from 50° C. to 100° C. for 3 hours;
(iii) cooling the reaction mixture obtained in (ii) to a temperature from 25° C. to 35° C., filtering, and washing with ethyl acetate solvent;
(iv) removing the solvent from the reaction mixture as obtained in (iii) under reduced pressure to obtain a fluorinated compound;
(v) purifying the fluorinated compound obtained in (iv) using flash chromatography by using 20% ethyl acetate in hexane eluent to obtain a pure fluorinated compound.

7. The process of claim 6, wherein the solvent used in (i) of the fluorination reaction is selected from acetonitrile or toluene.

8. The non-hygroscopic, thermally stable complex of claim 1, wherein the polysaccharide support is recyclable 4 times as a fluorinating agent.

\* \* \* \* \*